US009865054B2

United States Patent
Tsumura (10) Patent No.: US 9,865,054 B2
(45) Date of Patent: Jan. 9, 2018

(54) EVALUATION METHOD OF SPHEROID AND SPHEROID EVALUATION APPARATUS

(71) Applicant: SCREEN HOLDINGS CO., LTD., Kyoto (JP)

(72) Inventor: Jiro Tsumura, Kyoto (JP)

(73) Assignee: SCREEN HOLDINGS CO., LTD., Kyoto (JP)

(*) Notice: Subject to any disclaimer, the term of this patent is extended or adjusted under 35 U.S.C. 154(b) by 0 days.

(21) Appl. No.: 15/128,590

(22) PCT Filed: Dec. 1, 2014

(86) PCT No.: PCT/JP2014/081693
§ 371 (c)(1),
(2) Date: Sep. 23, 2016

(87) PCT Pub. No.: WO2015/145872
PCT Pub. Date: Oct. 1, 2015

(65) Prior Publication Data
US 2017/0358081 A1 Dec. 14, 2017

(30) Foreign Application Priority Data

Mar. 26, 2014 (JP) .................................. 2014-063860
Aug. 20, 2014 (JP) .................................. 2014-167074

(51) Int. Cl.
*G06T 7/00* (2017.01)
*G06T 7/64* (2017.01)
(Continued)

(52) U.S. Cl.
CPC ......... *G06T 7/0014* (2013.01); *G01N 21/253* (2013.01); *G01N 21/5907* (2013.01);
(Continued)

(58) Field of Classification Search
CPC ............. G06T 7/64; G06T 2207/10056; G06T 2207/30024; G01N 21/253; G01N 21/5907
See application file for complete search history.

(56) References Cited

U.S. PATENT DOCUMENTS

2003/0082516 A1  5/2003  Straus
2003/0143580 A1  7/2003  Straus
(Continued)

FOREIGN PATENT DOCUMENTS

JP  2005-502354 A  1/2005
JP  2009-225661 A  10/2009
(Continued)

OTHER PUBLICATIONS

Kenji Kawano et al., "Integrin α3β1 Engagement Disrupts Intercellular Adhesion," Experimental Cell Research 262 (2): 180-196 (2001).
(Continued)

*Primary Examiner* — Brenda Bernardi
(74) *Attorney, Agent, or Firm* — McDermott Will & Emery LLP (57) ABSTRACT

An evaluation method of a spheroid comprises specifying a spheroid region taken up by the spheroid out of the image including the spheroid and a surrounding region thereof, obtaining an average value of an optical density of the spheroid and a magnitude of a variation of the optical density in the spheroid from an image density of the spheroid region, obtaining a circularity of the spheroid from a contour of the spheroid region, obtaining a sharpness of the spheroid from the image densities of the spheroid and the surrounding region thereof, and obtaining the collapse degree of the spheroid by substituting the average value of the optical density, the magnitude of the variation of the
(Continued)

optical density, the circularity and the sharpness into a predetermined operational expression.

15 Claims, 6 Drawing Sheets

(51) Int. Cl.
    *G01N 21/59*     (2006.01)
    *G01N 21/25*     (2006.01)

(52) U.S. Cl.
    CPC ...... *G06T 7/64* (2017.01); *G06T 2207/10056* (2013.01); *G06T 2207/30024* (2013.01)

(56) References Cited

U.S. PATENT DOCUMENTS

| | | |
|---|---|---|
| 2003/0170613 A1 | 9/2003 | Straus |
| 2012/0134571 A1 | 5/2012 | Ito et al. |
| 2012/0142095 A1 | 6/2012 | Yano et al. |
| 2013/0076897 A1 | 3/2013 | Ogi et al. |
| 2014/0065655 A1* | 3/2014 | Itoh .................... G01N 33/5044 435/29 |
| 2016/0349240 A1* | 12/2016 | Fujimoto ........... G01N 33/5008 |

FOREIGN PATENT DOCUMENTS

| | | |
|---|---|---|
| JP | 2013-072684 A | 4/2013 |
| JP | 2014-010136 A | 1/2014 |
| WO | 2010/143420 A1 | 12/2010 |
| WO | 2011/016189 A1 | 2/2011 |
| WO | 2014/038025 A1 | 3/2014 |

OTHER PUBLICATIONS

A. Bru et al., "The effect of pressure on the growth of tumour cell colonies," Journal of Theoretical Biology, 243(2): 171-180 (2006).
Extended European Search Report issued in European Patent Application No. 14887324.3, dated Sep. 1, 2017.
Search Report issued in corresponding International Application No. PCT/JP2014/081693, dated Jan. 13, 2015.

* cited by examiner

EVALUATION METHOD OF SPHEROID AND SPHEROID EVALUATION APPARATUS

CROSS REFERENCE

This application is the U.S. National Phase under 35 US.C. §371 of International Application No. PCT/JP2014/081693, filed on Dec. 1, 2014, which claims the benefit of Japanese Application No. 2014-063860, filed on Mar. 26, 2014 and Japanese Application No. 2014-167074, filed on Aug. 20, 2014, the entire contents of each are hereby incorporated by reference.

TECHNICAL FIELD

This invention relates to an evaluation method and an evaluation apparatus for evaluating a collapse degree of a spheroid based on an image obtained by imaging the spheroid.

CROSS REFERENCE TO RELATED APPLICATION

The disclosure of Japanese Patent Applications enumerated below including specifications, drawings and claims is incorporated herein by reference in its entirety:
No. 2014-063860 filed on Mar. 26, 2014; and
No. 2014-167074 filed on Aug. 20, 2014.

BACKGROUND ART

A colony formation method is known as one of experiments for examining influences of a compound on cells. This method utilizes that cells may proliferate repeatedly to form a colony if a culture environment is proper. Specifically, cells are cultured in an environment where a compound as an evaluation target is added, and how the compound affects the life and death of the cells is evaluated from a count result on the number of colonies formed under such an environment (see, for example, patent literature 1). In this method, cell colonies two-dimensionally proliferated on a surface of an agar medium or the like are generally targets to be counted.

On the other hand, a three-dimensional culture is known as a culture method for cells closer to a living body. In this case, cultured cells are called a spheroid (cell aggregation) because they become a spherical aggregation. A spheroid is formed not only from the proliferation of one cell, but also from a plurality of cells gathering together. From this, it is necessary to judge a spheroid formation ability or a spheroid maintenance ability by a plurality of cells in the observation of a spheroid.

CITATION LIST

Patent Literature

Patent literature 1: JP2005-502354

SUMMARY OF INVENTION

Technical Problem

Since a spheroid has a three-dimensional structure, it is difficult to precisely judge its state only through observation from one direction. Thus, as a method for quantitatively evaluating a state of a spheroid, a reagent is added to a medium and light absorption or light emission caused by a biochemical reaction of cells are measured. However, measurement results largely vary in such a measurement and the reagent and the like are high in cost. In addition to that, since the spheroid is destroyed in the measurement, there has been a problem of being unable to continuously conduct the experiment.

Thus, it is desired to establish a technique for observing a state of a spheroid in a non-invasive manner and simply and precisely evaluating it. For example, it is considered to image an optical image of a spheroid and judge a state of the spheroid from that image. However, a technique for automatically evaluating a state of a spheroid by analyzing an image has not established yet and it is left to subjective judgment by an expert.

Solution to Problem

This invention was developed in view of the above problem and aims to provide a technique capable of objectively and stably evaluating a collapse degree of a spheroid from an image obtained by imaging the spheroid.

One aspect of this invention is directed to an evaluation method of a spheroid for evaluating a collapse degree of the spheroid from an image obtained by imaging the spheroid. The evaluation method comprises specifying a spheroid region taken up by the spheroid out of the image including the spheroid and a surrounding region thereof, obtaining an average value of an optical density of the spheroid and a magnitude of a variation of the optical density in the spheroid from an image density of the spheroid region, obtaining a circularity of the spheroid from a contour of the spheroid region, obtaining a sharpness of the spheroid from the image densities of the spheroid and the surrounding region thereof, and obtaining the collapse degree of the spheroid by substituting the average value and the magnitude of the variation of the optical density, the circularity and the sharpness into a predetermined operational expression.

Further, another aspect of this invention is directed to a spheroid evaluation apparatus for evaluating a collapse degree of a spheroid from an image obtained by imaging the spheroid. The evaluation apparatus comprises an image acquirer which obtains an image including the spheroid and a surrounding region thereof, an image processor which specifies a spheroid region taken up by the spheroid out of the image, obtains an average value of an optical density of the spheroid and a magnitude of a variation of the optical density in the spheroid from an image density of the spheroid region, obtains a circularity of the spheroid from a contour of the spheroid region and obtains a sharpness of the spheroid from the image densities of the spheroid and the surrounding region thereof, and a collapse degree calculator which calculates the collapse degree of the spheroid based on the average value and the magnitude of the variation of the optical density, the circularity and the sharpness.

In a spheroid having a high activity, a multitude of cells are bonded in a medium and this spheroid has a shape close to a sphere. In contrast, in weakened cells, a spheroid formation ability is lost and bonding between cells is weakened, whereby the spheroid collapses. Specifically, the shape of the spheroid cannot be maintained. Thus, it is convenient if a degree of that collapse can be quantitatively expressed. Conventionally, a collapse degree, which is a state change of the spheroid caused by the addition of a compound, has been subjectively judged by an expert through the direct observation of the spheroid, for example, by a microscope or the like or based on an image obtained by imaging the spheroid from a certain direction.

On the other hand, these inventions are configured to be able to objectively and stably evaluate the collapse degree of the spheroid by automatically quantifying the collapse degree of the spheroid from the image obtained by imaging the spheroid. Specifically, the average value and the magnitude of the variation of the optical density, the circularity and the sharpness are obtained for the spheroid region specified from the image and the collapse degree of the spheroid is obtained based on these pieces of information.

A spheroid composed of cells having a high activity has a sharp contour close to a circle. In contrast, a spheroid with advanced collapse has a collapsed shape and an unsharp contour. Further, living cells have a relatively light and uniform color, whereas dead cells have a dark color. Thus, a spheroid including dead cells has a high optical density as a whole and the variation of the optical density is also large.

These indices indicating the state of the spheroid can be quantitatively obtained from an image and the state of the spheroid can be objectively and stably evaluated in the invention by obtaining the collapse degree of the spheroid by calculation based on those values.

Advantageous Effects of Invention

According to the invention, the collapse degree of the spheroid is evaluated based on information mechanically derivable from the image of the spheroid. Thus, an objective and stable evaluation is possible without depending on the subjective judgment of a user.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

DESCRIPTION OF EMBODIMENTS

Figure 1:
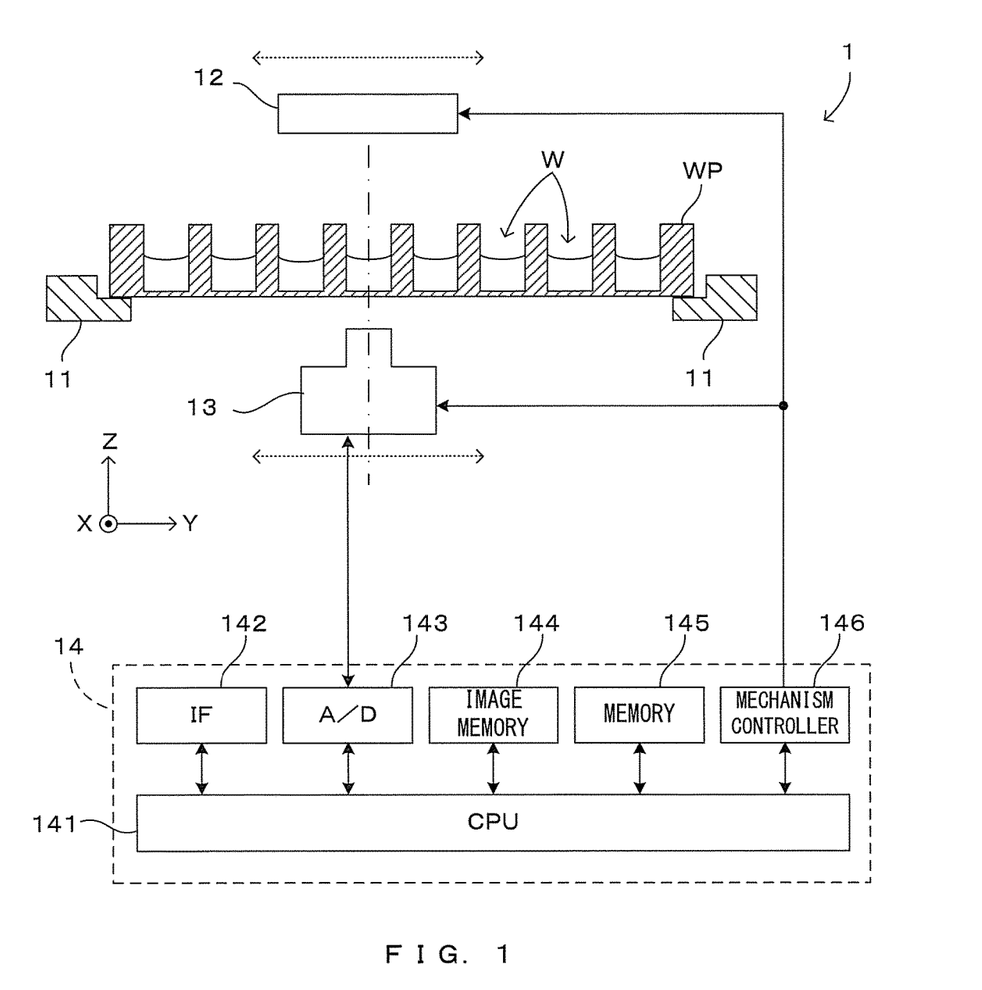
FIG. 1 is a diagram showing a schematic configuration of a spheroid evaluation apparatus according to the invention.

FIG. 1 is a diagram showing a schematic configuration of a spheroid evaluation apparatus (hereinafter, abbreviated to "evaluation apparatus") according to the invention. This spheroid evaluation apparatus 1 is an apparatus for imaging a spheroid (cell aggregation) cultured in liquid poured into recesses called wells W formed on the upper surface of a well plate WP and evaluating a collapse degree of the spheroid. For unified presentation of the directions in drawings, the XYZ orthogonal coordinate axes are established as shown in FIG. 1. The XY plane is a horizontal surface and the Z axis represents the vertical axis. In more detail, the (+Z) direction represents the vertically upward direction.

The well plate WP is generally used in the fields of drug discovery and bioscience. A plurality of wells W having a substantially circular cross-section and a transparent and flat bottom surface are disposed to the upper surface of a plate having a flat plate shape. The number of the wells W on the well plate WP is arbitrary. For example, a well plate WP having 96 (12×8 matrix array) wells can be used. A diameter and a depth of each well W are typically about several mm. Note that the size of a well plate and the number of wells used in this spheroid evaluation apparatus 1 are arbitrary without being limited to these. For example, well plate having 384 wells may be used.

A predetermined amount of liquid as a culture medium is poured into each well of the well plate WP. Spheroids cultured under predetermined culture conditions in this liquid are imaging objects of this imaging apparatus 1. The culture medium may be added with appropriate reagents or may be gelled after being poured into the wells W in a liquid state. About 50 to 200 microliters of the liquid is generally usually used. In this evaluation apparatus 1, for example, a spheroid cultured on an inner bottom surface of the well can be an imaging object as described later.

The evaluation apparatus 1 includes a holder 11 which holds the wellplate WP, an illuminator 12 arranged above the holder 11, an imager 13 arranged below the holder 11 and a controller 14 which includes a CPU 141 controlling the operation of these components. The holder 11 holds the well plate WP in a substantially horizontal posture by being held in contact with a peripheral edge part of the lower surface of the well plate WP carrying sample together with liquid in each well W.

The illuminator 12 emits appropriate diffused light (e.g., white light) toward the well plate WP held by the holder 11. More specifically, for example, a combination of a white LED (light emitting diode) as a light source and a diffusion plate may be used as the illuminator 12. The spheroids in wells W disposed to the well plate WP are illuminated by the illuminator 12 from above.

The imager 13 is provided below the well plate WP held by the holder 11. In the imager 13, an imaging optical system not shown in the figure is arranged at a position right below the well plate WP. An optical axis of the imaging optical system extends in a vertical direction (Z direction).

The imaging of the spheroid in the well W is performed by the imager 13. Specifically, light emitted from the illuminator 12 and incident on the liquid surface from above the well W illuminates the imaging object. Light transmitted downward from the bottom surface of the well W is incident to a light receiving surface of an imaging device not shown via the imaging optical system. An image of the imaging object is formed on the light receiving surface of the imaging device by the imaging optical system is imaged by the imaging device. A CCD sensor or a CMOS sensor can be used as the imaging device. Either a two-dimensional image sensor or a one-dimensional image sensor can be used.

The imager 13 is capable of moving in the XYZ directions by a mechanism controller 146 provided in the controller 14. Specifically, the mechanism controller 146 moves the imager 13 in the X direction and the Y direction based on a control command from the CPU 141. By doing so, the imager 13 moves in the horizontal direction. Further, focusing is performed by moving the imager 13 in the Z direction. When imaging is performed with the imaging object in a well W, the mechanism controller 146 positions the imager 13 in the horizontal direction such that the optical axis of the imaging optical system coincides with the center of the well W. When the imaging device of the imager 13 is a one-dimensional image sensor, a two-dimensional image can be obtained by scanning the imager 13 to an orthogonal direction to a longitudinal direction of the image sensor. By imaging in this manner, imaging can be performed in a non-contact, non-destructive and non-invasive manner with the spheroid as the imaging object, thereby damage to the spheroid caused by imaging can be suppressed.

Further, the as indicated by arrows with dotted lines shown in FIG. 1, mechanism controller 146 moves the illuminator 12 integrally with the imager 13 when the imager 13 is moved in the XY direction. Specifically, the illuminator 12 is arranged such that a center of emitted light substantially coincides with the optical axis of the imaging optical system. When the imager 13 moves in the XY direction, the illuminator 12 also moves in conjunction with the imager 13 in the XY direction. By doing so, whichever well W is imaged, the center of the well W and the center of emitted light are always position on the optical axis of the imaging optical system. Consequently, the illuminating condition becomes constant regardless of which well W is to be imaged, wherefore imaging conditions can be maintained to be satisfactory.

The image signal output from the imaging device of the imager 13 is send to the controller 14. Specifically, the image signal is input to an AD converter (A/D) 143 provided in the controller 14 and converted into digital image data. The CPU 141 performs appropriate image processings based on the received image data. The controller 14 further includes an image memory 144 for storing image data and a memory 145 for storing programs to be executed by the CPU 141 and data generated by the CPU 141, but these may be integrated. The CPU 141 performs variable calculation processings described later by executing a control program stored in the memory 145.

Besides, the controller 14 is provided with an interface (I/F) 142. The interface 142 has a function of performing data exchange with an external apparatus connected via a communication line besides a function of receiving an operation input from a user and presenting information such as processing results to the user. Note that the controller 14 may be an exclusive device including above hardware or may be a general-purpose processing device such as a personal computer or a workstation installed with the control program for performing the process described later. When a general-purpose processing device is used as the controller 14, the evaluation apparatus 1 may have just a minimal control function for controlling each components of the imager 13.

The evaluation apparatus 1 configured as described above is used to evaluate states of spheroids cultured in the wells W, more specifically the viability of the spheroids. For example, in the field of drug discovering screening, a compound as a drug candidate is administered to target cells such as cancer cells and changes of the target cells are observed. Particularly, in recent years, screening using a spheroid (cell aggregation) close to a state of cells in a living body has been required. The evaluation apparatus 1 of this embodiment can be suitably applied for such applications.

Which drug efficacy a compound exhibits to cells can be quantitatively expressed by a concentration of the compound necessary to inhibit cells, i.e. an inhibitory concentration (IC). Generally, the drug efficacy of the compound can be expressed by a half-inhibitory concentration (IC 50) which is a concentration that inhibits 50% of the cells administered with the compound. To this end, a technique for obtaining a cell survival rate after the administration of the compound is necessary.

In two-dimensionally cultured cells, living cells are proliferated to cause a growth of a cell colony, whereas dead cells do not form any colony. Accordingly, if the cells on which the compound was allowed to act form a colony, it indicates that those cells are alive. A "colony formation method" as a conventionally adopted screening method is a technique for utilizing this principle and estimating a cell survival rate by counting the number of formed colonies.

In contrast, in spheroids forming a three-dimensional structure by a multitude of cells already gathered together, even if cells die due to the drug efficacy, the number of the spheroids does not necessarily increase or decrease. In this case, the collapse of the spheroids occurs due to a decline of a spheroid formation ability of the cells. Thus, collapse degrees of the spheroids need to be quantitatively evaluated to obtain the cell survival rate.

Figure 2A:
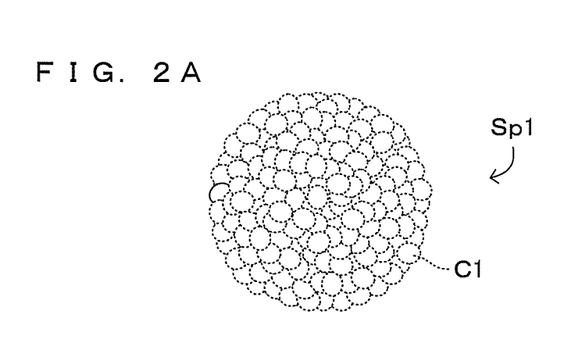
FIGS. 2A to 2C are diagrams schematically showing the external appearances of spheroids.

FIGS. 2A to 2C are diagrams schematically showing the external appearances of spheroids. A spheroid Sp1 shown in FIG. 2A is an example composed of cells with high viability. As shown, a shape close to a sphere is formed by cells C1 having a relatively light color. Thus, in a two-dimensional image obtained by imaging the spheroid Sp1, the contour of the spheroid Sp1 is substantially circular. Such a spheroid Sp1 can be said to have a low collapse degree.

Figure 2B:
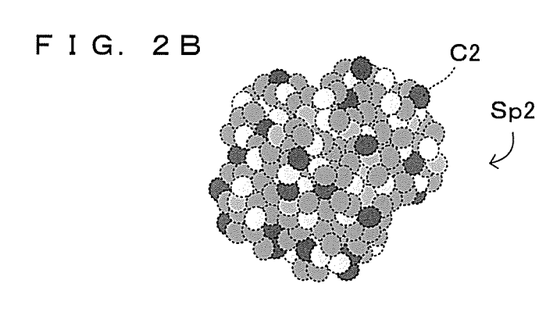

On the other hand, if some of cells constituting a spheroid die, the color of weakened or dead cells C2 becomes darker as in a spheroid Sp2 shown in FIG. 2B. Further, bonding forces between the cells are weakened and the contour of the spheroid Sp2 becomes indefinite. Such a spheroid Sp2 can be said to have a higher collapse degree than the spheroid Sp1. If the collapse further progresses, cells are gradually separated from a spheroid surface as in the spheroid Sp3 shown in FIG. 2C and the separated cells C3 are accumulated around the spheroid Sp3. Thus, the contour of the spheroid Sp3 itself becomes unsharp. A collapse degree of the spheroid SP3 in such a state can be said to be higher than that of the spheroid Sp2.

Figure 2C:
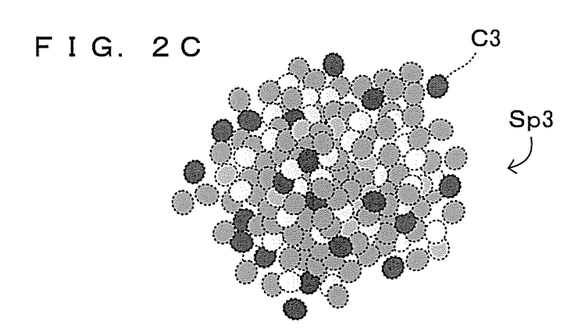

As just described, the collapse degree of the spheroid can be estimated to a certain degree by observing appearance changes such as the color and shape of the spheroid. However, how the collapse appears may differ depending on specimen preparation conditions such as cell species and the type of a substance to be administered and also may vary even under the same specimen preparation conditions. Thus, these appearance changes need to be comprehensively judged to properly evaluate the collapse degree. Such criteria have not been established yet and the collapse degree is subjectively determined through visual observation by a skilled determiner at present. Thus, a burden on the determiner is large and a variation of determination results is unavoidable.

The evaluation apparatus 1 is designed to quantitatively and stably evaluate a state of a spheroid with variations caused by the subjective view of a determiner eliminated by obtaining a collapse degree of the spheroid based on feature amounts of the spheroid quantitatively obtained from an image of the spheroid. A spheroid evaluation process using this evaluation apparatus 1 is described below.

Figure 3:
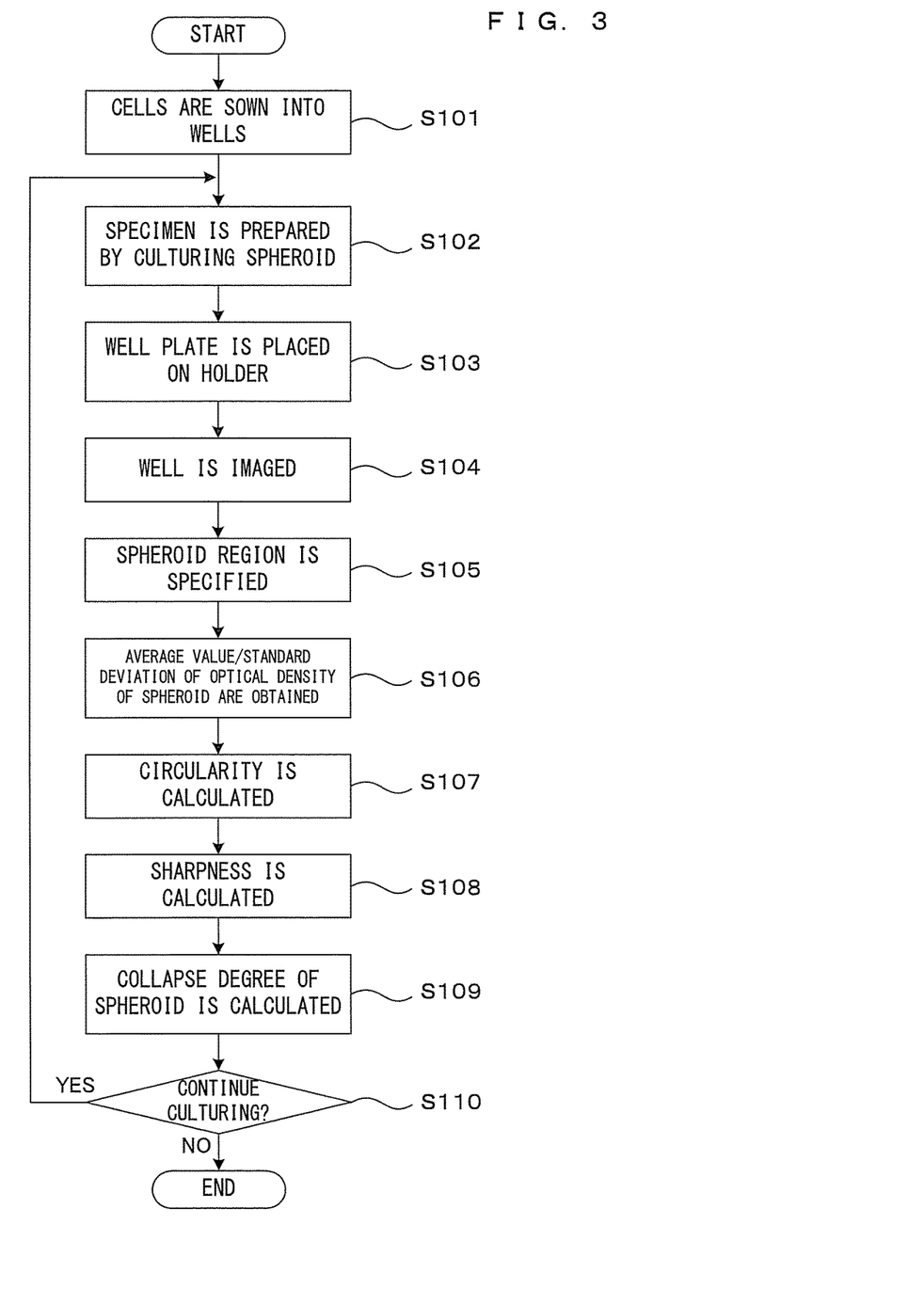
FIG. 3 is a flow chart showing the spheroid evaluation process in this embodiment.

FIG. 3 is a flow chart showing the spheroid evaluation process in this embodiment. In this process, a spheroid cultured in the well W of the well plate WP is imaged and a collapse degree of the spheroid is quantitatively obtained based on feature amounts obtained from that image. This process is performed by the CPU 141 provided in the control unit 14 operating each component of the apparatus based on the control program set in advance.

In this process, cells as evaluation targets are first sown into each well of the well plate WP (Step S101). Specifically, an appropriate medium is poured into each well W of the well plate WP and the cells are sown onto the medium. The well plate WP is held under a predetermined culture condition, for example, in an unillustrated incubator unit and a spheroid is cultured in each well W (Step S102). For the purpose of screening a compound as a drug candidate, the compound is added to each well W at a predetermined timing. In this way, a specimen including the spheroid as an evaluation target is prepared.

The well plate WP carrying the prepared specimens is placed on the holder 11 of the evaluation apparatus 1 at a necessary timing (Step S103). Then, the spheroid carried in each well W is imaged by the imager 13 (Step S104). In this embodiment, imaging is performed by causing illumination light to be incident from above the well W and receiving light transmitted through the bottom surface of the well W by the imager 13. However, an imaging method is arbitrary without being limited to this.

In this way, the spheroid in the well W is imaged. Subsequently, a region corresponding to the spheroid is extracted from the imaged image (Step S105). The spheroid region can be specified based on an image density difference between the spheroid and its surrounding background region included in the image. Specifically, an average image density of the entire image or a region estimatable as a background part of the entire image is obtained. A region in the image where an image density difference of each pixel from the average image density is larger than a predetermined threshold value can be regarded as the spheroid region. The medium corresponding to the background of the spheroid is generally colorless or in color lighter than the cells constituting the spheroid. Thus, by extracting a region having a relatively dark color in this way, the spheroid region can be separated from the background part and specified.

Note that, due to necessity to extract a contour part of the spheroid, the spheroid is desirably completely accommodated in a visual field of the image obtained by imaging the spheroid. That is, the imaged image preferably includes the entire spheroid and the background region surrounding the spheroid.

In the spheroid region in the image specified in this way, an optical density of this region and its variation (specifically, a standard deviation of the optical density) are obtained (Step S106). As described above, since the weakened cells change to have a darker color than the living cells, the presence of regions having a high optical density in the spheroid region indicates the weakening of the cells constituting the spheroid. Such a density change may appear in the entire spheroid region or may locally appear. Accordingly, an average value of the optical density in the entire spheroid region and a standard deviation indicating a variation of the optical density in the spheroid region are obtained as feature amounts representing the density of the spheroid region.

An average value OD of the optical density of the entire spheroid can be obtained, for example, from a luminance average value I1 of each pixel in the spheroid and a luminance average I2 of each pixel in the background region surrounding the spheroid by the following equation:

$$OD = \log_{10}(I2/I1).$$

Further, a standard deviation SD of the optical density can be, for example, obtained as a value of a standard deviation in a luminance value distribution of each pixel in a region other than a peripheral edge part in the spheroid region (e.g. spheroid center region having an area corresponding to 50% of the area of the spheroid area). Since a density variation is unavoidably large due to an imaging principle in the peripheral edge part of the spheroid, it is preferable to obtain a standard deviation in the center region excluding such a region.

Further, the circularity and the sharpness of the contour of the spheroid region are respectively calculated as feature amounts representing the contour shape of the spheroid in the image (Steps S107, S108). A circularity Cr of the spheroid can be, for example, obtained by the following equation when S denotes an area of the spheroid region in the image and L denotes a circumferential length of the contour of the spheroid:

$$Cr = 4\pi S/L^2.$$

Further, if the contour of the spheroid is sharp, it is considered that even a peripheral edge part in the spheroid region has a density equivalent to that of a central part. On the other hand, if the density is reduced in the peripheral edge part, the contour becomes unsharp. Thus, a sharpness Sh can be, for example, expressed by a value of an optical density ratio between the entire spheroid and its peripheral edge part. Specifically, the sharpness Sh can be expressed by the following equation:

$$Sh = ODp/OD.$$

Here, the value ODp is an optical density of the spheroid peripheral edge part and can be expressed from a luminance average value I3 in a peripheral region of the spheroid, specifically, for example, a spheroid internal region within a fixed range (e.g. a width corresponding to 10% of a diameter) from the contour of the spheroid and the luminance average value I2 of the background region by the following equation:

$$ODp = \log_{10}(I2/I3).$$

Further, the sharpness Sh may be defined using an edge intensity of the contour of the spheroid as below. If the spheroid has a sharp contour, an edge intensity of the contour, which is a boundary between the inside and the outside of the spheroid, is thought to be high in the image of the spheroid. From this, it is possible to express the sharpness using a value obtained by appropriately normalizing the edge intensity of the contour. For example, if a pixel having a pixel value corresponding to the edge intensity in the contour is virtually set as follows, a value of the optical density represented by the pixel value of this pixel can be used as a value indicating the sharpness.

First, the contour of the spheroid is extracted. Specifically, pixels located on a contour part of the spheroid (hereinafter, referred to as "contour pixels") out of pixels constituent the image are specified by an appropriate image processing. Since various known techniques are available as the image processing for contour extraction, no detailed description is given here. Note that the contour pixel is a pixel located on the boundary between the inside and the outside of the spheroid and the pixel itself belongs to the inside of the spheroid. In other words, the pixel in contact with the contour part of the spheroid and included in the spheroid in the image is specified as the contour pixel.

Subsequently, the edge intensity is calculated for the contour pixel obtained in this way. Various edge detection filtering processings can be applied as a processing for obtaining the edge intensity. For example, various filtering processings such as a Sobel filter, a differential filter, a Prewitt filter, a Roberts filter and a Laplacian filter can be suitably applied. Here is described a case where a Sobel filter operation is applied as an example of an edge detection filter.

A (3×3) Sobel filter operation is performed on a luminance value of each specified contour pixel. Coefficient matrices of the Sobel filter operation in a horizontal direction (x direction) and a vertical direction (y direction) of an image can be respectively expressed by the following equations.

$$X \text{ direction: } \begin{pmatrix} -1 & 0 & 1 \\ -2 & 0 & 2 \\ -1 & 0 & 1 \end{pmatrix}, \quad Y \text{ direction: } \begin{pmatrix} -1 & -2 & -1 \\ 0 & 0 & 0 \\ 1 & 2 & 1 \end{pmatrix}$$ [Equation 1]

Further, when Sx denotes a filter operation result in the x direction obtained for each contour pixel and Sy denotes an operation result in the y direction, an edge intensity Se of this contour pixel can be expressed by the following equation.

$$Se = \sqrt{Sx^2 + Sy^2}$$ [Equation 2]

The thus obtained value Se is a numerical value relatively expressing the edge intensity of the contour pixel in relation to the other pixels. In the principle of calculation, a scale of the luminance value is emphasized four-fold. Thus, by dividing the value of the edge intensity Se by 4, it is possible to obtain the edge intensity normalized to the same numerical value range of the scale as the luminance value of the pixel. If Sa denotes an average value of the edge intensities Se of the respective contour pixels belonging to one spheroid, a value (Sa/4) represents an average normalized edge intensity of the contour of the one spheroid and this serves as a value indicating the sharpness of the contour of this spheroid.

However, it is necessary to eliminate the influences of the density of the background region surrounding the contour of the spheroid and a variation of illumination conditions (shading). Accordingly, when a virtual image in which the contour pixels are replaced by pixels having the normalized edge intensity (Sa/4) obtained as described above as the luminance value is considered, the optical density of the contour pixel in this image is defined as the sharpness Sh of this spheroid. Specifically, the sharpness Sh is defined by the following equation:

$$Sh = \log_{10}\{Is/(Is - Sa/4)\}.$$

Here, a value Is is an average luminance value of the background region of the spheroid and the same as the average luminance value I2 described above. By expressing the sharpness by a dimension of the optical density taking into account the luminance of the background region, the influences of the background region of the spheroid and the illumination variation are eliminated and the sharpness Sh of each spheroid is objectively expressed. By doing so, a value of the sharpness Sh can be expressed as a numerical value comparable among different spheroids.

According to the knowledge of the inventor of this application, in the case of defining the sharpness Sh of the spheroid contour in this way, it was confirmed that the spheroid visually confirmed to have a clear contour in the image had a large value of the sharpness Sh, whereas the sharpness Sh had a value closer to 0 as the apparent unsharpness of the contour increased. Specifically, by the above definition, the sharpness of the spheroid contour can be quantitatively expressed with excellent accuracy highly correlated with a determination result of a skilled determiner.

As described above, each of the standard deviation SD of the optical density of the spheroid region, the average value OD of the optical density, the circularity Cr of the spheroid contour and the sharpness Sh of the spheroid contour is obtained as a feature amount representing a characteristic in appearance of the spheroid region in the imaged image. A collapse degree of the spheroid is calculated from each of the numerical values thus obtained (Step S109). A calculation method for that is described later.

For the specimens already imaged and having the collapse degree calculated, whether or not to continue the culturing is judged (Step S110). If the culturing is necessary, the specimens (specifically, well plate WP carrying the specimens) are returned to the incubator unit and continued to be cultured in the predetermined culture environment (Step S102). If it is not necessary to continue the culturing, the process is finished.

In this evaluation apparatus 1, the transmitted light of the illumination light irradiated to the specimen is detected by the imager 13 to image an optical image of the specimen (spheroid). In such an imaging method, the specimen can be imaged in a non-invasive manner and less damage is given to the specimen. Thus, it is possible to further culture the specimen subjected to imaging and observe a change of the shape of the spheroid with time. Therefore, so-called time-lapse imaging of imaging a change of the spheroid at each fixed time interval and the evaluation of the spheroid based on the imaging result are possible.

Next, a method for obtaining the collapse degree of the spheroid from the above feature amounts is described. How to quantify a spheroid collapse degree has not been clearly defined yet and depends on the subjective determination of an expert as described above. Accordingly, in this embodiment, a calculation equation (function) capable of indicating a high correlation with a determination result of an expert is defined using each feature amount (standard deviation SD of the optical density, average value OD of the optical density, circularity Cr and sharpness Sh) obtained as described above as an independent variable. Using this calculation equation, a collapse degree of an arbitrary spheroid is calculated.

Figure 4:
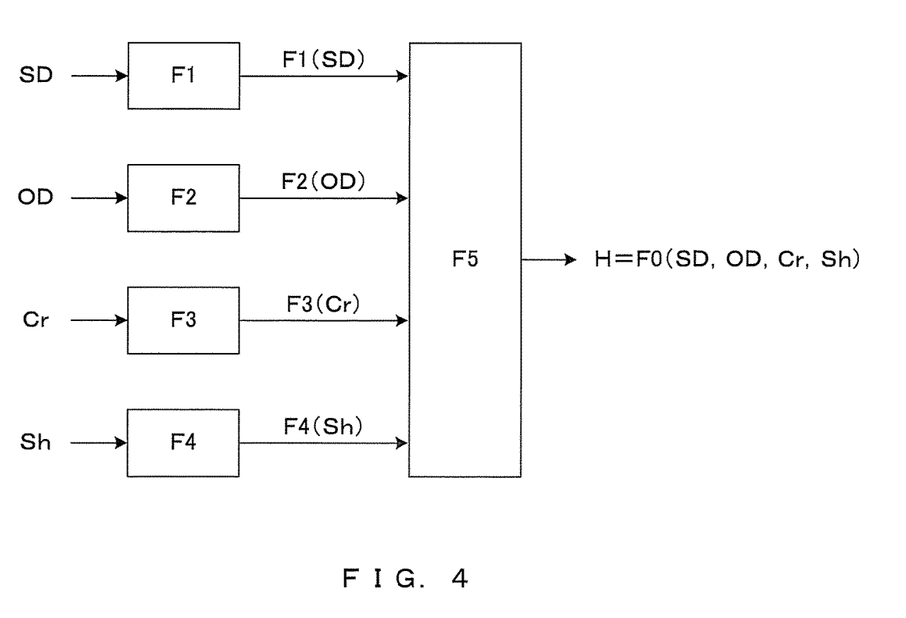
FIG. 4 is a diagram showing a concept of the collapse degree calculation equation.

FIG. 4 is a diagram showing a concept of the collapse degree calculation equation. A collapse degree H of a spheroid can be expressed by the following equation, using a function F0 which uses each of the above feature amounts (standard deviation SD of the optical density, average value OD, circularity Cr and sharpness Sh) as an independent variable:

$$H = F0(SD, OD, Cr, Sh) \quad \text{(Equation 1)}$$

However, in this embodiment, a value of each feature amount is applied to the calculation equation after being scaled to a fixed numerical value range. This is to avoid the cumbersomeness of calculation and an increase of an error due to different numerical value ranges of the respective feature amounts.

Specifically, as shown in FIG. 4, the collapse degree is expressed by the following equation by introducing functions F1, F2, F3 and F4 for scaling and a function F5 for making the feature amounts after scaling independent variables:

$$H1 = F5(F1(SD), F2(OD), F3(Cr), F4(Sh)) \quad \text{(Equation 2)}.$$

Note that although described in detail later, a value given on the right side of (Equation 2) indicates the collapse degree of the spheroid, but is not equal to the collapse degree H to be finally obtained in this embodiment. In that sense, the collapse degree is denoted by H1 here. The scaling of each feature amount can be appropriately determined such that a numerical value is 1 in the uncollapsed spheroid, in which each cell has a high activity, and increases as the collapse degree increases.

The scaling function F1 corresponding to the standard deviation SD of the optical density can be, for example, determined as follows. First, an ideal uncollapsed spheroid is assumed and a standard deviation of the optical density in this virtual spheroid is considered. Since the optical densities of the cells are not uniform, this standard deviation has a finite value larger than 0. In the ideal spheroid, an optical density variation among cells is very small. Accordingly, the standard deviation thereof is also a small value. On the other hand, a value of the standard deviation is thought to be large in actual spheroids. In that sense, the standard deviation SD of the optical density is thought to be smallest in the above virtual spheroid. Thus, the standard deviation of the optical density of this virtual spheroid is denoted by SDmin.

The scaling function F1 applied to actual spheroids may be a calculation equation to give a value which is closer to 1 if the spheroid is close to an ideal state and a variation of the optical density is small and to increase the value as the variation increases. For example, the scaling function F1 can be expressed by the following equation, using parameters i, p:

$$F1(SD) = \{i \times (SD - SDmin) + 1\}^p \quad \text{(Equation 3)}.$$

In this way, the collapse degree of the spheroid viewed in terms of the variation of the optical density is converted into a numerical value.

Next, the scaling function F2 corresponding to the average value OD of the optical density can be expressed by the following equation, using parameters j, q, for example, when ODmax denotes an optical density of an uncollapsed spheroid having a highest optical density:

$$F2(OD) = \{j \times (OD/ODmax - 1) + 1\}^q \quad \text{(Equation 4)}.$$

However, F2(OD) is uniformly 1 for spheroids whose average value OD of the optical density is not larger than ODmax.

Such a definition means as follows. A spheroid whose average value OD of the optical density is not larger than ODmax, i.e. whose optical density is lower than a fixed value can be regarded to have a high activity of cells and to be uncollapsed in terms of the optical density. Accordingly, a numerical value after scaling is 1. Spheroids whose optical density is higher than the above fixed value have a high possibility of including dead cells and (Equation 4) indicates a larger value as the optical density increases. In this way, the collapse degree of the spheroid viewed in terms of the optical density (average value) is converted into a numerical value.

The scaling function F3 corresponding to the circularity Cr of the spheroid gives a value of 1 for spheroids having a circularity not smaller than a threshold value m and, on the other hand, can be defined by the following equation, using parameters k, r for spheroids having a circularity smaller than the threshold value m:

$$F3(Cr) = \{k \times (m - Cr) + 1\}^r \quad \text{(Equation 5)}.$$

Similarly, the scaling function F4 corresponding to the sharpness Sh of the spheroid gives a value of 1 for spheroids having a sharpness not smaller than a threshold value n and, on the other hand, can be defined by the following equation, using parameters l, s for spheroids having a sharpness smaller than the threshold value n:

$$F4(Cr) = \{l \times (n - Sh) + 1\}^s \quad \text{(Equation 6)}.$$

The function F5 for obtaining the collapse degree from the feature amounts scaled as described above is thought to be, for example, such that the respective scaled feature amounts are multiplied by each other or added while being appropriately weighted. Specifically, either one of the following equations can be used:

$$F5 = \{F1(SD) \times F2(OD) \times F3(Cr) \times F4(Sh)\}^t \quad \text{(Equation 7)}$$

$$F5 = \{a \times F1(SD) + b \times F2(OD) + c \times F3(Cr) + d \times F4(Sh)\}^t \quad \text{(Equation 8)}.$$

Note that an index t is a parameter introduced to adjust an increasing tendency of the numerical value. Here, (Equation 8) is used, but (Equation 7) and (Equation 8) may be properly used according to the cell species and the state of the medium.

In expressing the collapse degree H by the function F0, it is necessary to determine the above parameters a, b, c, d, i, j, k, l, m, n, p, q, r, s and t. A method for theoretically and uniquely determining these has not been established yet. Accordingly, in this embodiment, each parameter is determined such that the collapse degree H obtained from the image of the spheroid by the above principle and the determination result on the collapse degree of the spheroid by an expert exhibit a high correlation. Specifically, each parameter can be, for example, determined as follows.

Figure 5:
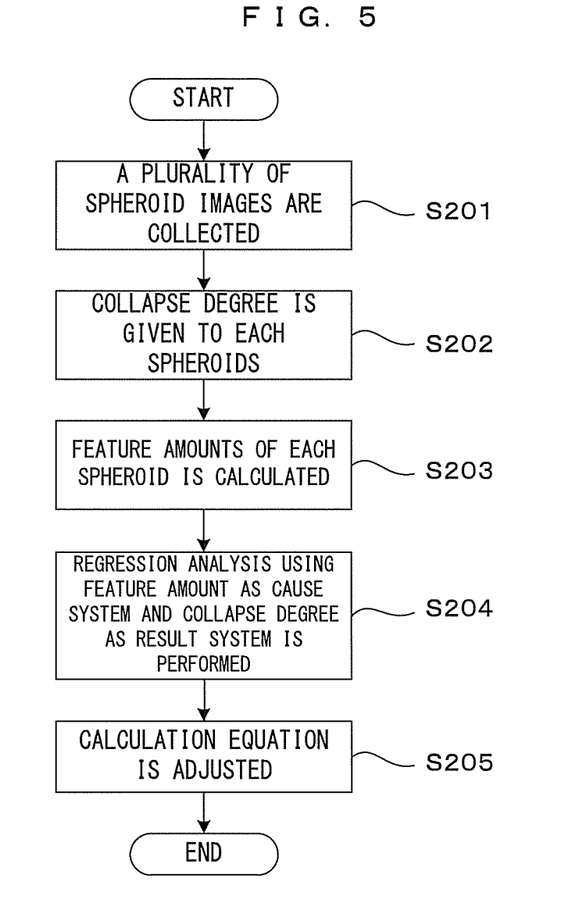
FIG. 5 is a flow chart showing a process of specifying a calculation equation for the spheroid collapse degree.

FIG. 5 is a flow chart showing a process of specifying a calculation equation for the spheroid collapse degree. First, a plurality of spheroid images having variously different collapse degrees are collected (Step S201). It is desirable to collect as many images as possible to enhance the accuracy of the calculation equation. To this end, spheroids may be cultured in advance, for example, by pouring the same type of medium into each well W of the well plate WP including a plurality of wells W and sowing the same type of cells into each well W and images obtained by imaging the cultured spheroids can be used. The spheroids cultured one by one in each well W may be imaged or a plurality of spheroids may be cultured in one well W and each may be individually imaged. Further, spheroid images imaged in the past for the same cell species and the same medium may be collected.

Then, collapse degrees are given to the spheroids in the collected images by the determination of an expert (Step S202). The collapse degree can be, for example, in four grades of 0, 1, 2 and 3. A collapse degree of 0 is given to the spheroids judged not to have been collapsed, whereas a larger numerical value is given as the collapse degree increases. Note that the classification of the collapse degree is arbitrary without being limited to classification into four grades.

From the collected images, the feature amounts of each spheroid, i.e. the standard deviation SD and the average value OD of the optical density, the circularity Cr and the sharpness Sh are obtained (Step S203). Then, each parameter in the above equations is obtained such that the value of the function F5 obtained by substituting each calculated feature amount SD, OD, Cr, Sh into (Equation 8), i.e. the collapse degree H, matches the value given in Step S202. For example, by performing a regression analysis using the feature amounts SD, OD, Cr and Sh obtained for each of the plurality of images as a cause system and the given collapse degrees as a result system (Step S204), each parameter in the above equations can be determined. There are various known methods for the regression analysis and those known techniques can be applied also to this embodiment. Thus, they are not described. Further, a calculation equation may be specified based on various machine learning techniques.

In this way, the parameters a, b, c, d, i, j, k, l, m, n, p, q, r, s and t of the calculation equation expressing the collapse degree H are determined. Then, also for a spheroid having a collapse degree not determined yet, the collapse degree can be calculated based on the feature amounts of this spheroid and the calculation equation in principle. However, the calculation equation is further adjusted as follows in this embodiment (Step S205).

To match the numerical value of the collapse degree H obtained by calculation with the determination result of the expert, the collapse degree H needs to be expressed in a numerical value range of 0 to 3. However, spheroids as evaluation targets have a relatively large individual variation and the determination result possibly varies also when the determiner gives the collapse degree to the spheroid in Step S202. Thus, the numerical value range of the results of the calculation equation obtained in a state including those variations may not necessarily be 0 to 3. Normalization to correct this is necessary.

Figure 6A:
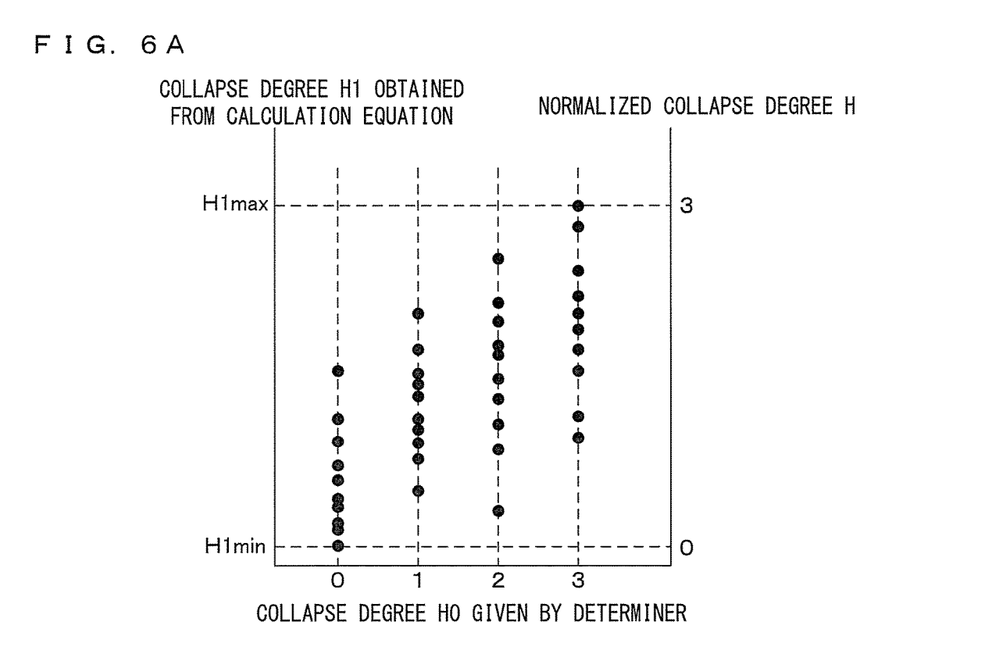
FIGS. 6A and 6B are graphs showing the principle of normalizing the collapse degree.
Figure 6B:
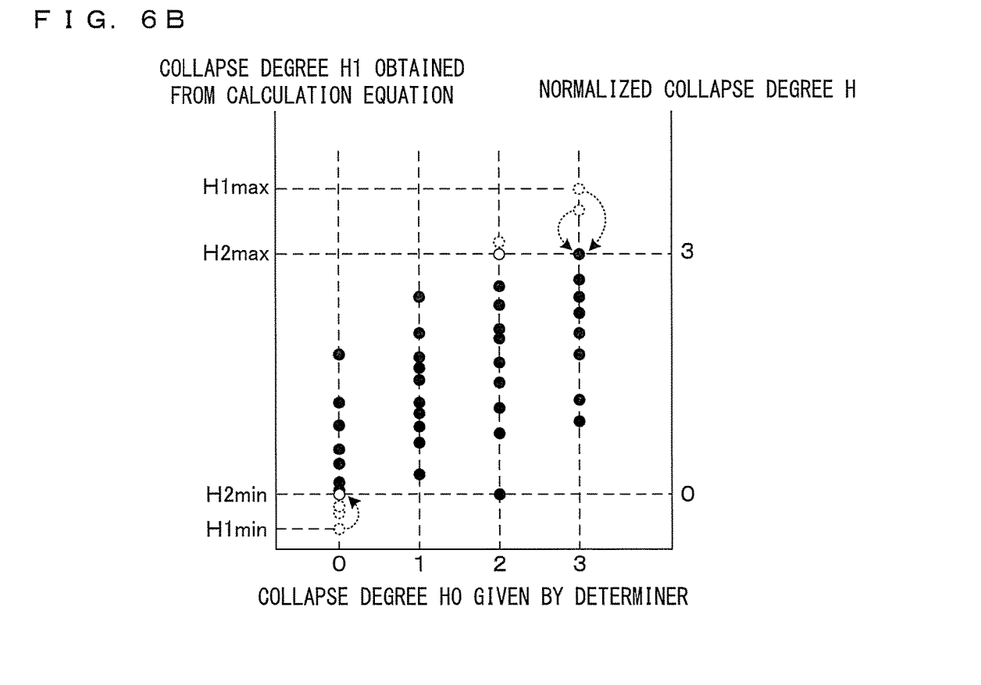

FIGS. 6A and 6B are graphs showing the principle of normalizing the collapse degree. Collapse degrees H0 of spheroids given by a determiner for a plurality of spheroid images and collapse degrees H1 of the spheroids obtained from the calculation equation (function F5) specified by the regression analysis are plotted in an H0-H1 space. Then, as shown in FIG. 6A, the collapse degrees H1 obtained by the same calculation equation for the spheroids having variously different appearance characteristics vary to a certain extent. In normalizing these collapse degrees H1 and obtaining a final collapse degree H, normalization may be performed in principle that the collapse degree H=3 may be correlated with a maximum value H1max of the collapse degree by calculation and the collapse degree H=0 may be correlated with a minimum value H1min.

However, the values of H1 calculated for the respective spheroids in this way possibly include abnormal values due to image noise or erroneous determination of the determiner. Accordingly, in this embodiment, the collapse degrees H1 lying in a fixed range (e.g. upper 10%) from the largest one out of the collapse degrees H1 obtained by calculation for a plurality of spheroids are all substituted by a next value H2max as shown in FIG. 6B. Those having small values out of the collapse degrees H1, e.g. values of lower 10% are also similarly substituted by a next value H2min. That is, if H2 denotes the collapse degree after substitution, the following classification is obtained:

$H2 = H2\max$ when $H1 > H2\max$, $H2 = H2\min$ when $H1 < H2\min$, and $H2 = H1$ when $H2\min \leq H1 \leq H2\max$.

The collapse degree H=3 is correlated with the maximum value H2max after substitution and the collapse degree H=0 is correlated with the minimum value H2min of the collapse degree. By such normalization, the collapse degrees H of all the spheroids can be expressed in the numerical value range of 0 to 3 and, in addition, a reduction in the accuracy of calculation due to data having a protruding value is also avoided.

In calculating the collapse degree H for an arbitrary spheroid, the feature amounts SD, OD, Cr and Sh are obtained for this spheroid and the value H1 is calculated based on those values and the functions F1 to F5 with the determined parameters. If the calculated value H1 is above H2max or below H2min, the value H2 is obtained by rounding down or up the calculated value H1 to H2max or H2min, respectively.

The collapse degree H is finally obtained by substituting this value H2 into the following equation obtained from the relationship of FIG. 6B:

$$H = 3 \times (H2 - H2\min)/(H2\max - H2\min) \quad \text{(Equation 9).}$$

Here, a constant 3 on the right side is a normalization coefficient for expressing the collapse degree H by a value of 0 to 3. In this embodiment, the normalization coefficient is set at 3 to correspond to four grades of 0 to 3 of the determination of the collapse degree by the determiner.

More generally, when the collapse degree is expressed in z grades, the collapse degree H can be obtained as a value of 0 to (z−1) by the following equation:

$$H = (z-1) \times (H2 - H2\min)/(H2\max - H2\min) \quad \text{(Equation 10).}$$

Here, H2 is a value obtained by substituting the values of the feature amounts SD, OD, Cr and Sh of the spheroid into the above (Equation 1) to (Equation 8) and the right side of (Equation 10) is nothing but the function F0 having the feature amounts SD, OD, Cr and Sh as independent variables.

As is clear from the above theoretical development, the larger the variation of the optical density of the spheroid, the larger the value of the collapse degree, and the larger the average value of the optical density of the spheroid, the larger the value of the collapse degree according to (Equation 10). Further, the lower the circularity of the spheroid contour, the larger the value of the collapse degree, and the lower the sharpness of the spheroid contour, the larger the value of the collapse degree.

Note that the appearance characteristics of the spheroid differ depending on the cell species and the state of the medium. Thus, the above calculation equations based on the feature amounts of the spheroid need to be specified for each cell species or for each state of the medium. The calculation equation specified for each cell species or for each state of the medium in this way can be applied to spheroids cultured under the same conditions (cell species and medium). Thus, the collapse degree can be objectively and stably obtained from the feature amounts of the spheroid without depending on the subjective view of the determiner. Note that a method for changing only parameters while using the calculation equation in the same format and a method for making the format of the calculation equation itself different are considered in defining a different calculation equation.

As described above, in the spheroid evaluation apparatus 1 of the above embodiment, the holder 11 functions as a "holder" of the invention, the imager 13 functions as an "imager" of the invention and these integrally function as an "image acquirer" of the invention. The CPU 141 functions as an "image processor" and a "collapse degree calculator" of the invention.

As described above, an operational expression for obtaining the collapse degree in the invention can be, for example, obtained by collecting a plurality of spheroid images having numerical values indicating the collapse degrees given thereto and performing the regression analysis using the average value and the magnitude of the variation of the optical density, the circularity and the sharpness of the spheroid obtained for each of the collected images as a cause system and the numerical values of the collapse degrees of the images as a result system.

The collapse degree of the spheroid needs to be comprehensively judged from various perspectives and it is, at present, difficult to uniquely determine the collapse degree itself only from objective numerical values. On the other hand, an expert can determine the collapse degree with relatively high reproducibility through the visual observation of the spheroid image. Accordingly, for a plurality of spheroid images, each image and a collapse degree, for example, determined in advance by an expert may be associated and such an operational expression that the value of the collapse degree obtained by the calculation of the average value and the magnitude of the variation of the optical density, the circularity and the sharpness of the spheroid obtained from each image and the value of the collapse degree associated with this image match with a high probability may be derived.

The regression analysis is known as a method for specifying such an operational expression. Specifically, the operational expression for associating the cause system and the result system can be specified by performing the regression analysis using the average value and the variation of the optical density, the circularity and the sharpness of the spheroid as the cause system and the values of the collapse degrees associated with the images as the result system. Regression analysis methods have been conventionally studied and an evaluation result highly correlated with the judgment of an expert can be obtained without depending on subjective judgment by determining the operational expression by applying those methods.

From the aforementioned optical characteristics of the spheroid, the operational expression is desirably such that the higher the average value of the optical density of the spheroid, the higher the collapse degree; the larger the variation of the optical density of the spheroid, the higher the collapse degree; the smaller the circularity of the spheroid, the higher the collapse degree; and the smaller the sharpness of the spheroid, the higher the collapse degree. These are conditions for reflecting the scientific knowledge on the collapse of the spheroid on the operation result. Note that which value is given in expressing the height of the collapse degree in numerical value is not particularly limited. For example, a large numerical value may be given as the collapse degree to the spheroid with advanced collapse or may be vice versa. Further, the collapse degrees may be expressed stepwise by discrete numerical values.

Further, the sharpness of the spheroid can be, for example, defined as a value of a ratio of the optical density of a peripheral edge part of the spheroid and the optical density of the entire spheroid. In the spheroid with the sharp contour, an optical density equivalent to that of the central part is maintained up to the peripheral edge part of the spheroid. However, in the spheroid with the unsharp contour, i.e. the spheroid having an ambiguous boundary between the spheroid and the surrounding region, the optical density of the peripheral edge part tends to be lower than that of the central part. Thus, it can be understood that the contour is sharp if the value of the ratio of the optical density of the peripheral edge part of the spheroid and that of the entire spheroid is close to 1, and becomes more unsharp as the value becomes smaller.

Further, the sharpness of the spheroid may be, for example, defined as the optical density of a pixel having a pixel value corresponding to an edge intensity in the contour of the spheroid region. More specifically, when Sa denotes an average value of edge intensities obtained for the respective pixels corresponding to the contour of the spheroid region based on luminance values of the pixel values by an edge detection filter operation and Is denotes an average value of luminances of pixels in the region surrounding the spheroid, the sharpness may be defined as the left side Sh of the following equation:

$$Sh = \log_{10}\{Is/(Is - Sa/4)\}.$$

As described above, the collapse degree of the spheroid can be more accurately evaluated by introducing the sharpness based on such a definition.

Further, the operational expression may be differently configured, for example, according to the cell species forming the spheroid. Since the color and the shape of the spheroid and characteristics of changes appearing with collapse differ depending on the cell species, it is difficult to define a single operational expression for various cell species. If it is possible to define different operational expressions according to the cell species, a plurality of cell specifies can be dealt with. Further, a different operational expression may be defined for each cell culture method.

Further, in the spheroid evaluation apparatus according to this invention, the image acquirer may include, for example, a holder which holds a container for carrying a medium including spheroids and an imager which images the spheroids in the container held by the holder and obtaining images. According to such a configuration, the imaging of the spheroids and the evaluation of the collapse degree can be perfoir led by a single apparatus.

In this case, the imager preferably images the spheroids in a non-invasive manner. According to such a configuration, it is possible to continue to culture specimens (spheroids) after imaging. For example, how the same spheroid changes with time can be evaluated.

Further, for example, the image acquirer may be configured to receive image data of spheroids imaged by an external imaging device or stored in an external storage device. Specifically, the spheroid evaluation apparatus according to the invention is not limited to the one having itself an imaging function and may only evaluate based on image data given from outside. According to such a configuration, the evaluation function described above can be given by combining the spheroid evaluation apparatus, for example, with an existing imaging apparatus.

Note that the invention is not limited to the above embodiment and various changes other than those described above can be made without departing from the gist of the invention. For example, the calculation equation described above is an example of a calculation method applicable to the technical concept of the invention and the applied calculation equation is arbitrary without being limited to the above one.

Further, in the above embodiment, the height of the collapse degree is expressed by the magnitude of the numerical value and the collapse degree is so defined that the numerical value of the collapse degree increases as the collapse of the spheroid progresses. However, contrary to this, the collapse degree may be expressed by such an index that the numerical value becomes smaller as the collapse progresses.

Further, in the above embodiment, the collapse degree is defined to take a continuous value according to the state of the spheroid without being limited to a discrete numerical value. By doing so, spheroids having higher collapse degrees and those having lower collapse degrees can be quantitatively classified, for example, even among the spheroids having the same discrete collapse degree. However, the calculation equation may be so defined that the collapse degree obtained by calculation takes a numerical value in one of many discrete grades similarly to determination by the determiner. To enable this, the calculation equation may be, for example, so adjusted as to round up the numerical value of the collapse degree obtained by calculation and use only an integer part as a result.

Further, in the above embodiment, illumination light is incident on the well W from above the well plate WP held in a horizontal posture and the light transmitted through the bottom surface of the well W is received by the imager 13 to perform imaging. However, the invention is characterized in the processing of the imaged spheroid image and the imaging principle of the image may be arbitrary without being limited to the above one. However, images by bright-field imaging are preferable.

Further, for example, the imager 13 is used as the "image acquirer" of the invention in the above embodiment. However, it is not essential that the spheroid evaluation apparatus according to the invention itself has an imaging function. Specifically, image data imaged by an external imaging device or stored and saved in an external storage device may be received and only the image processing may be performed. In this case, the interface 142 for receiving the image data from outside functions as the "image acquirer" of the invention.

In this case, an already commercialized imaging apparatus can be utilized. Accordingly, the spheroid evaluation apparatus of the invention can be configured, for example, by combining a general-purpose personal computer installed with the control program for performing the process according to the invention with the imaging apparatus. Thus, the invention can be provided as a control program to be installed in a personal computer combined with an imaging apparatus besides being able to be embodied as a complete apparatus as in the above embodiment.

Further, in the above embodiment, it is aimed to specify the calculation equation for such a collapse degree as to match a subjective determination result of an expert. However, such a calculation equation as to exhibit a high correlation with an evaluation result by another evaluation method such as an ATP assay or an MTT assay may also be obtained.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

INDUSTRIAL APPLICABILITY

This invention can be applied for the purpose of quantitatively evaluating a collapse degree of a cultured spheroid and can be utilized, for example, in quantitatively evaluating the drug efficacy of a compound allowed to act on a spheroid for the purpose of drug discovery screening.

REFERENCE SIGNS LIST 1 spheroid evaluation apparatus
11 holder (holder)
13 imager (imager, image acquirer)
141 CPU (image processor, collapse degree calculator)
142 interface
Sp1, Sp2, Sp3 spheroid
W well
WP well plate (container)

The invention claimed is:

1. An evaluation method of a spheroid for evaluating a collapse degree of the spheroid from an image obtained by imaging the spheroid, the evaluation method comprising:
  specifying a spheroid region taken up by the spheroid out of the image including the spheroid and a surrounding region thereof;
  obtaining an average value of an optical density of the spheroid and a magnitude of a variation of the optical density in the spheroid from an image density of the spheroid region;
  obtaining a circularity of the spheroid from a contour of the spheroid region;
  obtaining a sharpness of the spheroid from the image densities of the spheroid and the surrounding region thereof; and
  obtaining the collapse degree of the spheroid by substituting the average value of the optical density, the magnitude of the variation of the optical density, the circularity and the sharpness into a predetermined operational expression.

2. The evaluation method of the spheroid according to claim 1, wherein the operational expression is determined by collecting a plurality of spheroid images having numerical values indicating the collapse degrees given thereto and performing a regression analysis using the average value of the optical density, the magnitude of the variation of the optical density, the circularity and the sharpness of the spheroid obtained for each of the collected images as a cause system and numerical values of the collapse degrees of the images as a result system.

3. The evaluation method of the spheroid according to claim 1, wherein the operational expression is such that the higher the average value of the optical density of the spheroid, the higher the collapse degree.

4. The evaluation method of the spheroid according to claim 1, wherein the operational expression is such that the larger the variation of the optical density of the spheroid, the higher the collapse degree.

5. The evaluation method of the spheroid according to claim 1, wherein the operational expression is such that the smaller the circularity of the spheroid, the higher the collapse degree.

6. The evaluation method of the spheroid according to claim 1, wherein the operational expression is such that the smaller the sharpness of the spheroid, the higher the collapse degree.

7. The evaluation method of the spheroid according to claim 1, wherein the sharpness of the spheroid is defined as a value of a ratio of the optical density of a peripheral edge part of the spheroid and an optical density of a whole of the spheroid.

8. The evaluation method of the spheroid according to claim 1, wherein the sharpness of the spheroid is defined as an optical density of a pixel having a pixel value corresponding to an edge intensity in the contour of the spheroid region.

9. The evaluation method of the spheroid according to claim 8, wherein when Sa denotes an average value of edge intensities obtained for respective pixels corresponding to the contour of the spheroid region based on luminance values of the pixel values by an edge detection filter operation and Is denotes an average value of luminances of pixels in the region surrounding the spheroid, the sharpness is defined as a left side Sh of a following equation:

$$Sh=\log_{10}\{Is/(Is-Sa/4)\}.$$

10. The evaluation method of the spheroid according to claim 1, wherein the operational expression is differently configured according to cell species forming the spheroid.

11. A spheroid evaluation apparatus for evaluating a collapse degree of a spheroid from an image obtained by imaging the spheroid, the evaluation apparatus comprising:
an image acquirer which obtains an image including the spheroid and a surrounding region thereof,
an image processor which specifies a spheroid region taken up by the spheroid out of the image, obtains an average value of an optical density of the spheroid and a magnitude of a variation of the optical density in the spheroid from an image density of the spheroid region, obtains a circularity of the spheroid from a contour of the spheroid region and obtains a sharpness of the spheroid from the image densities of the spheroid and the surrounding region thereof, and
a collapse degree calculator which calculates the collapse degree of the spheroid based on the average value of the optical density, the magnitude of the variation of the optical density, the circularity and the sharpness.

12. The spheroid evaluation apparatus of claim 11, wherein
the collapse degree calculator performs a regression analysis using the average value of the optical density, the magnitude of the variation of the optical density, the circularity and the sharpness of the spheroid obtained from each of a plurality of images in which the spheroid and a value indicating its collapse degree are correlated each other as a cause system and numerical values of the collapse degrees of the images as a result system and calculates the collapse degree of the spheroid based on an operational expression obtained as a result of the regression analysis, the average value of the optical density, the magnitude of the variation of the optical density, the circularity and the sharpness of the spheroid.

13. The spheroid evaluation apparatus of claim 11, wherein
the image acquirer comprises:
a holder which holds a container for carrying a medium including spheroids; and
an imager which images the spheroids in the container held by the holder and obtains the images.

14. The spheroid evaluation apparatus of claim 13, wherein the imager images the spheroids in a non-invasive manner.

15. The spheroid evaluation apparatus of claim 11, wherein the image acquirer receives image data of spheroids imaged by an external imaging device or stored in an external storage device.

* * * * *